United States Patent
Prinzhofer et al.

(10) Patent No.: US 7,588,943 B2
(45) Date of Patent: Sep. 15, 2009

(54) METHOD FOR QUANTITATIVE MONITORING OF A GAS INJECTED IN A RESERVOIR IN PARTICULAR IN A NATURAL ENVIRONMENT

(75) Inventors: Alain Prinzhofer, Paris (FR); Alexandre Rojey, Malmaison (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 857 days.

(21) Appl. No.: 10/484,834

(22) PCT Filed: Jul. 24, 2002

(86) PCT No.: PCT/FR02/02643

§ 371 (c)(1),
(2), (4) Date: Jan. 26, 2004

(87) PCT Pub. No.: WO03/010534

PCT Pub. Date: Feb. 6, 2003

(65) Prior Publication Data

US 2004/0166582 A1 Aug. 26, 2004

(30) Foreign Application Priority Data

Jul. 26, 2001 (FR) .................................. 01 10050

(51) Int. Cl.
*G01N 33/24* (2006.01)
*G01N 33/22* (2006.01)
*G01N 30/02* (2006.01)
*G01N 24/00* (2006.01)
*G01N 37/00* (2006.01)

(52) U.S. Cl. .............................. 436/27; 436/28; 436/56; 436/161; 436/173; 436/181; 436/182

(58) Field of Classification Search ............. 436/27–28, 436/56–57, 161, 173, 181–182
See application file for complete search history.

(56) References Cited

U.S. PATENT DOCUMENTS 2,318,689 A * 5/1943 Hodell et al. ............ 166/252.6
2,578,500 A * 12/1951 Savoy et al. ................... 436/27
3,993,131 A * 11/1976 Riedel ........................... 436/27
4,055,399 A * 10/1977 Parrish .......................... 436/27
4,617,994 A * 10/1986 Richardson ................. 166/300
4,722,394 A * 2/1988 Wellington et al. ..... 166/250.12
4,928,522 A   5/1990 Tonnelli
4,972,704 A   11/1990 Wellington
5,111,882 A * 5/1992 Tang et al. ................ 166/252.6
5,501,273 A * 3/1996 Puri ......................... 166/252.5
5,881,807 A   3/1999 Bae
6,234,004 B1  5/2001 Revsbech et al.
6,321,595 B1 * 11/2001 Pope et al. ................ 73/152.39

FOREIGN PATENT DOCUMENTS

DE 4323283 7/1993
EP 0816631 1/1998

OTHER PUBLICATIONS

Karacan, C. O. et al, Fuel 2001, 80, 509-520.*
Egsgaard, H. et al, Analytica Chimica Acta 1987, 199, 265-270.*
Anderson, R. P. et al, Oil & Gas Journal 1989, 87(15), 44-46,48,50-51.*

* cited by examiner

*Primary Examiner*—Arlen Soderquist
(74) *Attorney, Agent, or Firm*—Antonelli, Terry, Stout & Kraus, LLP.

(57) ABSTRACT

A method for quantitative monitoring of a gas injected into a reservoir and likely to react chemically with the injection medium includes injecting into a reservoir a mixture of the potentially reactive gas to be quantified with a low proportion of a tracer gas whose chemical inertness is total, and in determining the variation with time of the initial proportion of reactive gas that may have disappeared through conversion, by measuring the concentration variation of the tracer gas in the mixture. The tracer gas is preferably selected from the rare gas family and from isotopes thereof, unlikely to be contaminated by contact of the mixture with the injection medium, and which have physical properties such as solubility in water or diffusion coefficients as close as possible to the gas injected. The method is applicable to monitoring of the evolution and conversion of a reactive gas such as carbon dioxide or methane, injected into an underground reservoir for example.

11 Claims, 2 Drawing Sheets

FIG.1
|  | Solubilité | Diffusion (cm²/s x10⁻⁵) | Produit |
|---|---|---|---|
| $CH_4$ | 2,80167E-05 | 1,67 | 4,6788E-05 |
| $CO_2$ | 0,000702835 | 1,92 | 0,001349444 |
| He | 7,02222E-06 | 6,28 | 4,40995E-05 |
| Ne | 8,34838E-06 | 3,01 | 2,51286E-05 |
| Ar | 2,73261E-05 | 1,98 | 5,41057E-05 |
| Kr | 5,03317E-05 | 1,92 | 9,66369E-05 |
| Xe | 8,80091E-05 | 1,85 | 0,000162817 |
FIG.2
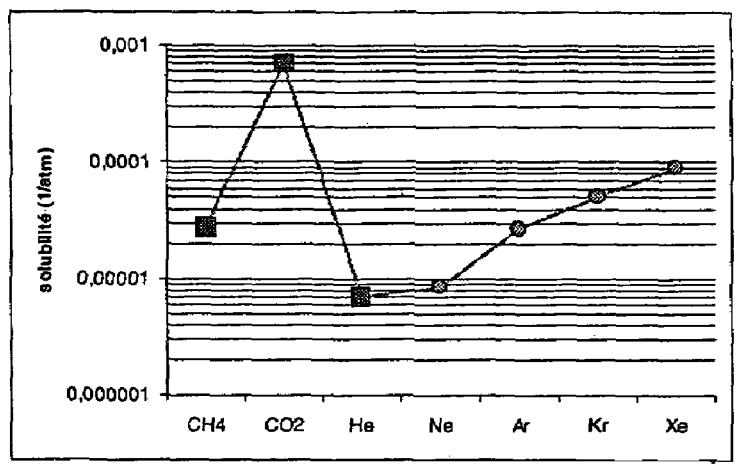
FIG.3
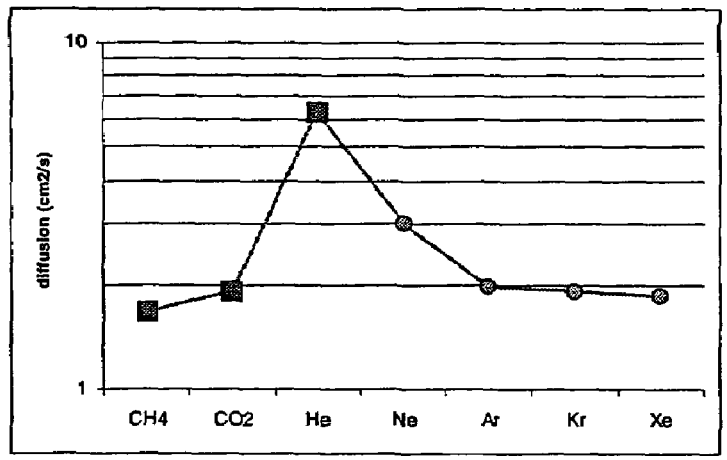

METHOD FOR QUANTITATIVE MONITORING OF A GAS INJECTED IN A RESERVOIR IN PARTICULAR IN A NATURAL ENVIRONMENT

FIELD OF THE INVENTION

The present invention relates to a method allowing quantitative monitoring of a gas injected into a reservoir such as a natural medium.

The method finds applications in many fields where the gas injected in the reservoir is likely to react chemically with the injection medium.

It allows for example to quantify the fraction of a gas injected into an underground reservoir which has reacted chemically with the surrounding medium in relation to the fraction of gas whose chemical form has not changed. During storage of natural hydrocarbon gases for distribution flexibility reasons, the recovery of this gas is never perfect. Part of this gas (mainly methane) may either remain sequestered in certain compartments of the reservoir, or react under a chemical or bacterial action and be converted to another gaseous species or a solid.

Another field of application is for example the sequestration of carbon dioxide in underground reservoirs: mine roads, coal banks or ancient oil reservoirs. It is desirable that part of this $CO_2$ can be converted to solids (carbonates for example) in order to definitively eliminate the risk of its taking part in the greenhouse effect by discharge to the atmosphere. The method proposed allows to quantify the proportion of $CO_2$ converted to a solid in the course of time, insofar as it is possible to take injected gas samples after injection has been completed.

SUMMARY OF THE INVENTION

The method essentially consists in injecting into a reservoir a mixture of the potentially reactive gas to be quantified with a relatively low proportion of a tracer gas whose chemical inertness is total, and in determining the variation with time of the initial proportion of reactive gas that may have disappeared through conversion, by measuring the concentration variation of the tracer gas in the mixture.

The tracer gas can be selected, for example, from rare gases free from contamination problems and which have physical properties such as solubility in water or diffusion coefficients as close as possible to the gas injected.

The tracer gas can be selected, for example, from rare gas isotopes which are non-contaminable and have physical properties (such as solubility in water or diffusion coefficients) as close as possible to the gas injected, determining the variation with time of the initial proportion of reactive gas that may have disappeared through conversion comprising a concentration measurement by isotopic dilution.

The method comprises for example injecting into the reservoir a mixture of methane and of a rare gas such as argon.

The method can also comprise for example injecting into the reservoir a mixture of carbon dioxide and of a rare gas such as xenon or krypton.

Measurement of the variation with time of the initial proportion of reactive gas can be carried out by gas chromatography, by quadrupole spectrometry or by coupling a preparation line to a magnetic spectrometer.

BRIEF DESCRIPTION OF THE FIGURES

Other features and advantages of the method according to the invention will be clear from reading the description hereafter, with reference to the accompanying drawings wherein:

FIG. 1 is a chart of the solubility values for two reactive species: methane and carbon dioxide, and for the rare gas family species (He, Ne, Ar, Kr, Xe), FIG. 2 shows the solubility values expressed as inverses of Henry's constant in $atm^{-1}$ for the two reactive species ($CH_4$, $CO_2$) and for the same rare gas family, FIG. 3 shows, in form of a graph, the values (in $cm^2 s^{-1}$) of the diffusion coefficients in water for the two reactive species ($CH_4$, $CO_2$) and for the same rare gas family species.

DETAILED DESCRIPTION

Figure 4:
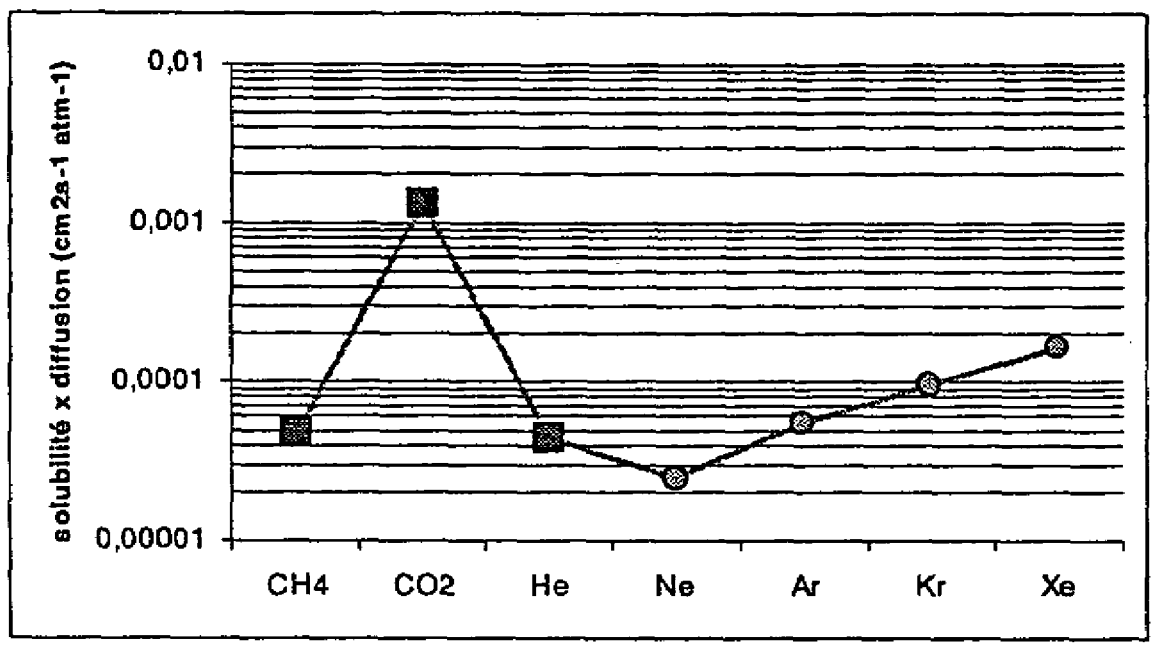
FIG. 4 shows, in form of a graph, the product of the solubility by the diffusion coefficient, in the same units as in FIGS. 1, 2, for the same reactive species and the same rare gas family species.

The method comprises, as mentioned above, injecting into a reservoir such as an underground reservoir a mixture of the potentially reactive gas to be quantified with a relatively low proportion of another species (a tracer gas) whose chemical inertness is total, and measuring the variation with time of the initial proportion of the reactive gas that may have disappeared through conversion.

The two conceivable physical processes that affect the reactive species and the rare gas tracer are the solubilization of the gas in water and the diffusion of the molecular gaseous species in water. In fact, diffusion in the gas phase can be considered to be negligible given the times considered between each sampling (months or years). Another important factor for these carrying dissolution phenomena is the product of the solubility by the diffusion, as described for example by:

Krooss B. M. (1992): Diffusive Loss of Hydrocarbons through Cap Rocks. Erdöl & Kohle-Erdgas-Petrochemie/Hydrocarbon Technology, 45, p.387-396.

The chart in FIG. 1 gives, for the two reactive species considered (methane and carbon dioxide) and for the rare gas family, the values of the solubility coefficients in soft water at 20° C. and 1 atm. gas, the diffusion coefficients of these species in water, and the product of these two parameters. The values of these parameters will be different for other temperatures, pressures and compositions of the aqueous phase, but by first approximation, these variations will be of the same order for all the species considered, and the ratios between species, which alone interest us, will remain practically identical.

It appears that the rare gas whose physical properties are the closest to those of methane is argon. The high solubility of $CO_2$ in water corresponds to no rare gas, xenon being the gas which is the closest thereto. However, xenon being a rare gas that is readily adsorbed on solids, we recommend using krypton, whose properties are close to the properties of xenon and which is affected to a lesser degree by this adsorption trapping problem.

Calculation of the quantity to be injected in relation to the analysis accuracy and the accuracy on the proportion of injected gas having reacted chemically The proportion of rare gas to be injected in methane or carbon dioxide depends on the analytical accuracy considered and on the precautions to be taken with the contamination by air and the aquifers surrounding the storage site. In fact, the argon contents of air are close to 1%, the aquifers are also very rich in argon, which requires using either a more concentrated tracer (but concentrations above 1% are against the quality of the gas injected), or using a less abundant isotope of argon (36Ar or 38Ar). For krypton tracing, the contents in air are much lower (X ppm), and the contamination problem is less. Contamination is understood to be the change in the initial proportion of rare gas in relation to the injected mixture of the same tracer gas by contact with the injection medium. The advantage of tracing by means of a rare gas whose isotopic composition is different from that of air (or of the natural media concerned by storage) is that it allows both to avoid contamination problems and to carry out measurements by isotopic dilution, which are the most accurate measurements available to date. The analysis method used can be, by increasing the sensitivity and the result accuracy, gas chromatography (only sensitive to chemical species, without isotope distinction), quadrupole spectrometry (same limitation but higher sensitivity) or coupling of a preparation line to a magnetic spectrometer, which allows precise measurement of the concentrations and of the abundance ratios. The quantity of gas that has reacted chemically after injection can be calculated with the following formula:

$$Q = T(R - R_o)$$

where Q=quantity of gas that has reacted, T=quantity of tracer injected, $R_o$=ratio between the quantity of gas and of tracer at the time of the injection, R=ratio between the quantity of residual gas and of tracer at the time of a sampling operation. One can consider that the measuring accuracy of a ratio R is routinely of the order of some percents, which gives an equivalent accuracy on the estimation of the quantity of gas that has reacted chemically. If the measurement is performed by chromatography, the sensitivity limit of a standard chromatograph equipped with a TCD detector is about 0.1%, so that the carbon dioxide to be injected will have to contain one volume of krypton for at least 1000 volumes of carbon dioxide. As for argon, we have seen that tracing by means of a mixture of isotopes in a proportion that is different from that in the natural media is essential. The chromatography analysis method (and the quadrupole spectrometry method) is therefore not suitable.

If a magnetic isotopic spectrometer is used, it is possible to use tracers of different isotopic composition, which improves the measuring quality and reduces the quantities to be injected. For example, a tracer essentially consisting of 38Ar would have a cumulative effect with the atmospheric contents of about $5 \cdot 10^{-6}$. An injection up to $20 \cdot 10^{-6}$ (mole/mole) would therefore be perfectly sufficient. For krypton, 78Kr for example, which has a $4 \cdot 10^{-9}$ concentration in the atmosphere, could be used in a proportion of $10^{-6}$ allowing easy measurement, without having to take account of the pollution by the surrounding medium.

Implementation

The method can be used to test an underground site in order to determine its gas storage ability. In this case, a slim hole is drilled down to the zone to be tested and a homogeneous mixture of gas and of tracer gas is injected for a relatively short time, of the order of some days to some months. The samples required for measurement of the tracer proportion variation in the mixture injected at the end of the residence time thereof are taken by opening a valve in the injection hole.

The method can also be used to monitor the evolution of the content of a gas reservoir under development so as to detect variations in the composition of a mixture injected therein. Measurement of the variation of the tracer gas proportion in carbon dioxide allows for example to monitor its possible conversion to carbonates on contact with the medium. The well used for sampling can be different from the well through which the gas is injected.

The sampling frequency after injection, within the scope of this monitoring operation, can range between some months and some years.

The invention claimed is:

1. A method for quantitative monitoring of a gas injected into an underground reservoir, likely to react chemically with the underground reservoir, comprising:
    selecting a tracer gas whose chemical inertness is total, wherein the tracer gas is a rare gas unlikely to be contaminated by contact of the mixture with the underground reservoir, and which has solubility in water and diffusion coefficient as close as possible to those of the gas injected;
    injecting into the reservoir a mixture of the gas with an initial proportion of the tracer gas;
    measuring a variation with time of the proportion of tracer gas in the mixture, after injection of the mixture; and
    determining a quantity of the gas that may have disappeared when the gas reacts chemically with the underground reservoir, from the measured variation of the proportion of the tracer gas with time as compared to the initial proportion.

2. A method as claimed in claim 1, characterised in that the rare gas is a gas isotope unlikely to be contaminated by contact of the mixture with the underground reservoir, and which has physical properties as close as possible to those of the gas injected, determination of the variation with time of the proportion of the reactive gas comprising a concentration measurement by isotopic dilution.

3. A method as claimed in claim 1, characterised in that the gas comprises methane.

4. A method as claimed in claim 3, characterized in that the selected tracer gas is argon.

5. A method as claimed in claim 1, characterised in that the gas comprises carbon dioxide.

6. A method as claimed in claim 5, characterized in that the tracer gas is xenon or krypton.

7. A method as claimed in claim 1, characterised in that measurement of the variation with time of the proportion is carried out by gas chromatography.

8. A method as claimed in claim 1, characterised in that measurement of the variation with time of the proportion is carried out by quadrupole spectrometry.

9. A method as claimed in claim 1, characterised in that measurement of the variation with time of the proportion is carried out by coupling a preparation line to a magnetic spectrometer.

10. Application of the method as claimed in claim 1 for evaluation of the gas storage ability of an underground zone.

11. Application of the method as claimed in claim 1 for monitoring of an underground reservoir used for gas storage.

* * * * *